US00PP10751P

United States Patent [19]

de Belder

[11] Patent Number: Plant 10,751

[45] Date of Patent: Jan. 12, 1999

[54] *HYDRANGEA PANICULATA* 'RUBY'

[75] Inventor: Jelena de Belder, Hemelryck, Belgium

[73] Assignee: Monrovia Nursery Company, Azusa, Calif.

[21] Appl. No.: 844,797

[22] Filed: Apr. 22, 1997

[51] Int. Cl.[6] ..... A01H 5/00

[52] U.S. Cl. ..... Plt./67.1

[58] Field of Search ..... Plt./67.1

*Primary Examiner*—James R. Feyrer

[57] ABSTRACT

A new and distinct selection of Panicle Hydrangea which shall be referred to hereinafter as *Hydrangea paniculata* cultivar Ruby. *Hydrangea paniculata* cultivar Ruby differs distinctively from other *Hydrangea paniculata* plants by its unique combination of daintier, graceful growth habit and smaller more numerous showy sterile flower sepals and dark autumn color of flower sepals.

2 Drawing Sheets

BACKGROUND OF THE INVENTION

The present invention relates to a new and distinct selection of *Hydrangea paniculata* a member of the Saxifragaceae family. *Hydrangea paniculata* cv. Ruby was the result of three generations of field selection. The first generation was my selection *Hydrangea paniculata* 'Unique', a seedling that originated from the well known *Hydrangea paniculata* 'Floribunda'. *Hydrangea paniculata* 'Floribunda' main attribute is numerous sterile flowers with showy sepals. The second generation was a seedling derived from *Hydrangea paniculata* 'Unique' named *Hydrangea paniculata* 'Pink Diamond'. *Hydrangea paniculata* 'Ruby' resulted as a seedling from *Hydrangea paniculata* 'Pink Diamond' after three years of field observation in flower. I selected *Hydrangea paniculata* cv. 'Ruby' in 1992. My discovery was made at my residence in Hemelryck, 2910 Essen, Belgium. Selection was based on the attributes of smaller daintier habit, numerous showy sepals and dark autumn colored flower sepals.

My new plant has been asexually reproduced by cuttings since the discovery in 1992 at my residence in Hemelryck, 2910 Essen, Belgium and later at Monrovia Nursery Company, 13455 S.E. Lafayette Highway, Dayton, Oreg. Had the seedling not been discovered and propagated it may have been lost to mankind. It is unlikely these select and favorable attributes of this plant could be conveyed to progeny through sexual reproduction in the next generation. However, throught extensive propagation by rooting of the plant it has been established that the novel exceptional characteristics of this plant are stable and reliably passed on to clonal specimens through asexual reproduction.

SUMMARY OF INVENTION

*Hydrangea paniculata* cv. 'Ruby' has a more graceful and smaller growth habit than the generations it was derived from and other *Hydrangea paniculata* plants to my knowledge. Typically, *Hydrangea paniculata* can reach of size of 5 meters tall to 3.5 meters wide. Cultivar 'Ruby' has not exceeded a size of 2 meters tall×2 meters wide. Along with the smaller size is a more daintier and graceful appearance.

My new selection has smaller showy flower bracts (sepals) but more numerous in amount. My selection displays more compact and diminutive flower panicles which begin to bloom in summer. The sepal color is a creamy white. In Belgium starting in September through October the sepal color begins to take on a blush red tinge and later deepens to a rose pink. Other selections do not exhibit an autumn sepal color as dark as cultivar Ruby.

Cultivar Ruby has tolerated −25° C., which is equivalent to a U.S.D.A. hardiness zone four with no harm or damage.

BRIEF DESCRIPTION OF DRAWINGS

The accompanying photographs exhibit the inflorescence.

One photograph shows the creamy white color of the early season bloom. The showy sterile florets are enhanced by the small fertile background florets.

The other photograph displays an inflorescence, exposed to cooler weather that has taken on a blush red tinge and is beginning to deepen to a rose pink color.

BOTANICAL DESCRIPTION

Below is a detailed description of *Hyrdangea paniculata* cv. 'Ruby', the color terminology is from the British Horticultural Color Charts.

Overall habit: Deciduous broad-leaved shrub.

Overall size: Rounded with equal height to width ratio, ultimate size estimated to two meter tall and two meters wide.

Foliage:

- *Arrangement.*—Opposite.
- *Pubescence.*—Sparsely setose on upper leaf. Sparsely pubsecent on veins beneath.
- *Shape.*—Overall — simple and elliptic. Base — rounded and obtuse. Tip — abrupt, acuminate.
- *Margins.*—Lower half of leaf — serrulate. Upper half of leaf — serrate.
- *Size.*—Length — 10–12 cm. Width — 5.6–7 cm.
- *Petiole.*—Length 1.2–2 cm.
- *Color.*—Upper leaf surface: Lavender Green 000761 changing with cold weather to Purple Madder 1028/3. Underside of leaf: Spinach Green 0960/3.

Flowers:

- *Arrangement.*—Terminal panicle.
- *Size of panicle.*—Range from 9–20 cm long and 10–15 cm.wide.
- *Number within panicle.*—Numerous.
- *Fertile flowers.*—The 'non-showy' flower lacking petals (sepals) tend to be situated within and at the tip of the panicle.
- *Sterile flowers.*—The 'showy' flowers. Petals: Number — normally 4. Color — creamy white, Primrose Yellow 601 changing with age and cold weather to Fuchsia Purple 28/1, 28/2, 28/2, 28/3, with Amaranth Rose 530,530/1, 530/2, 530/3. Size: 2–2.5 cm long and as wide.

Fruit: a dried capsule, not observed to date.

I claim:

1. A new and distinct selection of *Hydrangea paniculata* plant substantially as shown and described which differs distinctively from other *Hydrangea paniculata* plants by its unique combination of daintier, graceful growth habit and smaller more numerous showy sterile flower sepals and dark autumn color of flower sepals. .

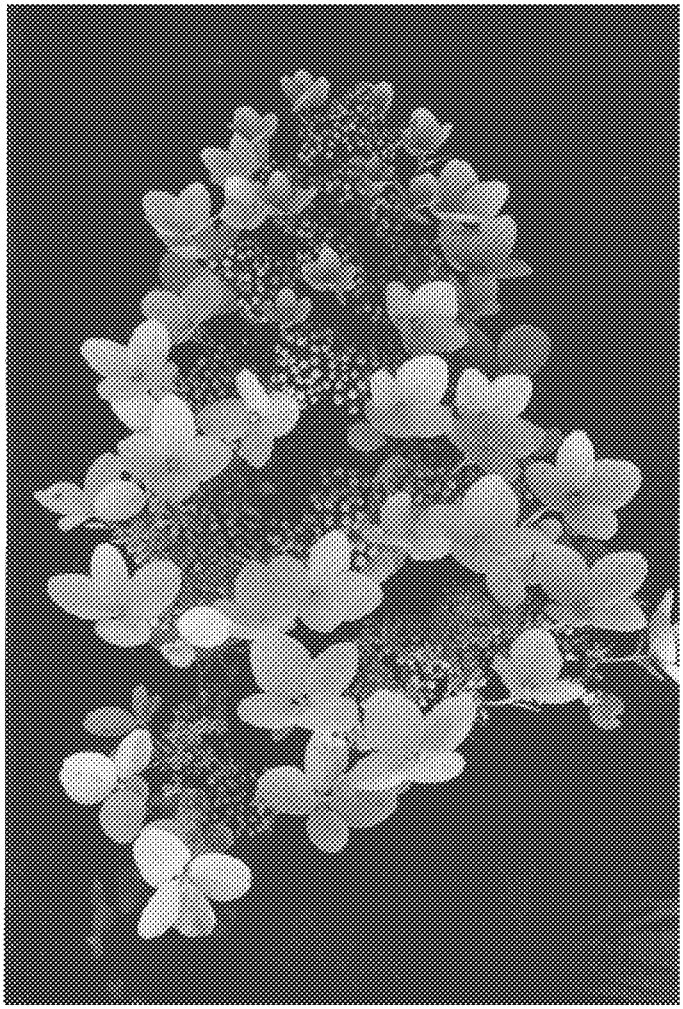

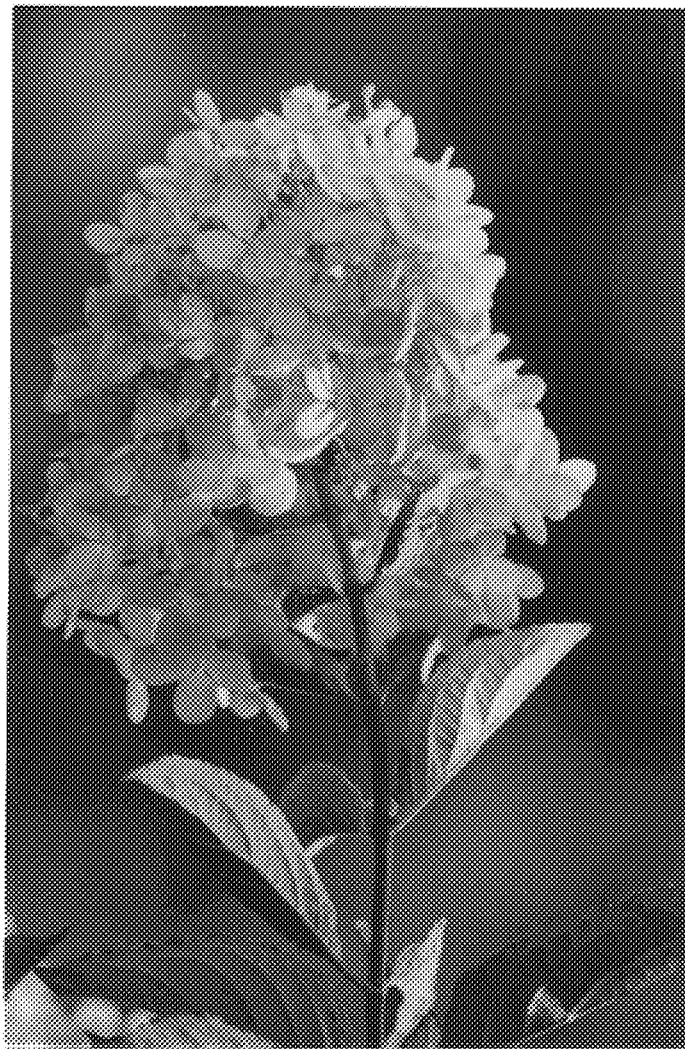

* * * * *